United States Patent [19]

Heifetz

[11] 4,165,745
[45] Aug. 28, 1979

[54] SURGICAL MANIPULATOR

[76] Inventor: Milton D. Heifetz, 704 No. Bedford Dr., Beverly Hills, Calif. 90210

[21] Appl. No.: 794,471

[22] Filed: May 6, 1977

[51] Int. Cl.$^2$ ................. A61B 17/32; A61B 17/28; A61B 17/06

[52] U.S. Cl. ................. 128/318; 30/191; 30/252; 81/43; 128/321; 128/340; 128/354

[58] Field of Search ............. 128/354, 322, 321, 346, 128/340, 318, 303 R; 81/43, 302; 30/252, 244, 250, 239, 191, 192, 193

[56] References Cited

U.S. PATENT DOCUMENTS

| | | | |
|---|---|---|---|
| 966,325 | 8/1910 | Gilbert | 81/43 |
| 2,749,615 | 6/1956 | Griffon | 30/252 X |
| 3,367,336 | 2/1968 | Eizenberg | 128/354 X |
| 3,446,211 | 5/1969 | Markham | 128/322 |
| 3,805,792 | 4/1974 | Cogley | 128/346 X |
| 4,020,846 | 5/1977 | Stokes | 128/354 X |

OTHER PUBLICATIONS

Catalogue Illustration of Storz Needle Holder, E-3790, E-3972, and E-3793.

*Primary Examiner*—Robert W. Michell
*Assistant Examiner*—Michael H. Thaler
*Attorney, Agent, or Firm*—Donald D. Mon

[57] ABSTRACT

A surgical manipulator useful to apply compressively opposed forces and enable the surgeon to rotate the manipulator and the article it is applied to, with minimal lateral wobble and tremor.

The manipulator comprises a pair of prongs, each of which supports a jaw with an operative element such as a needle holder, tissue pickup, nipper or scissors. The prongs are resiliently biased by bias means away from one another in a plane of flexure to spread the operative elements apart, and the prongs can be closed by force exerted on manipulation surfaces carried by the prongs. A spindle includes a knuckle rest which is closer to the joinder of the prongs than the manipulation surfaces. The knuckle rest bears against a knuckle (defined to include the muscle pad between the thumb and the index finger) when the device is held by the surgeon with his thumb and index finger on respective manipulation surfaces. The manipulation surfaces, when the jaws are brought together, form a substantially regular geometric surface circumferentially around a central axis which is no more out of round than a hexagon, and which the surgeon can rotate by relative movement of the thumb and index finger. The knuckle rest surface is unsplit, and is also a substantially regular geometric surface circumferential around the axis no more out of round than a hexagon.

14 Claims, 24 Drawing Figures

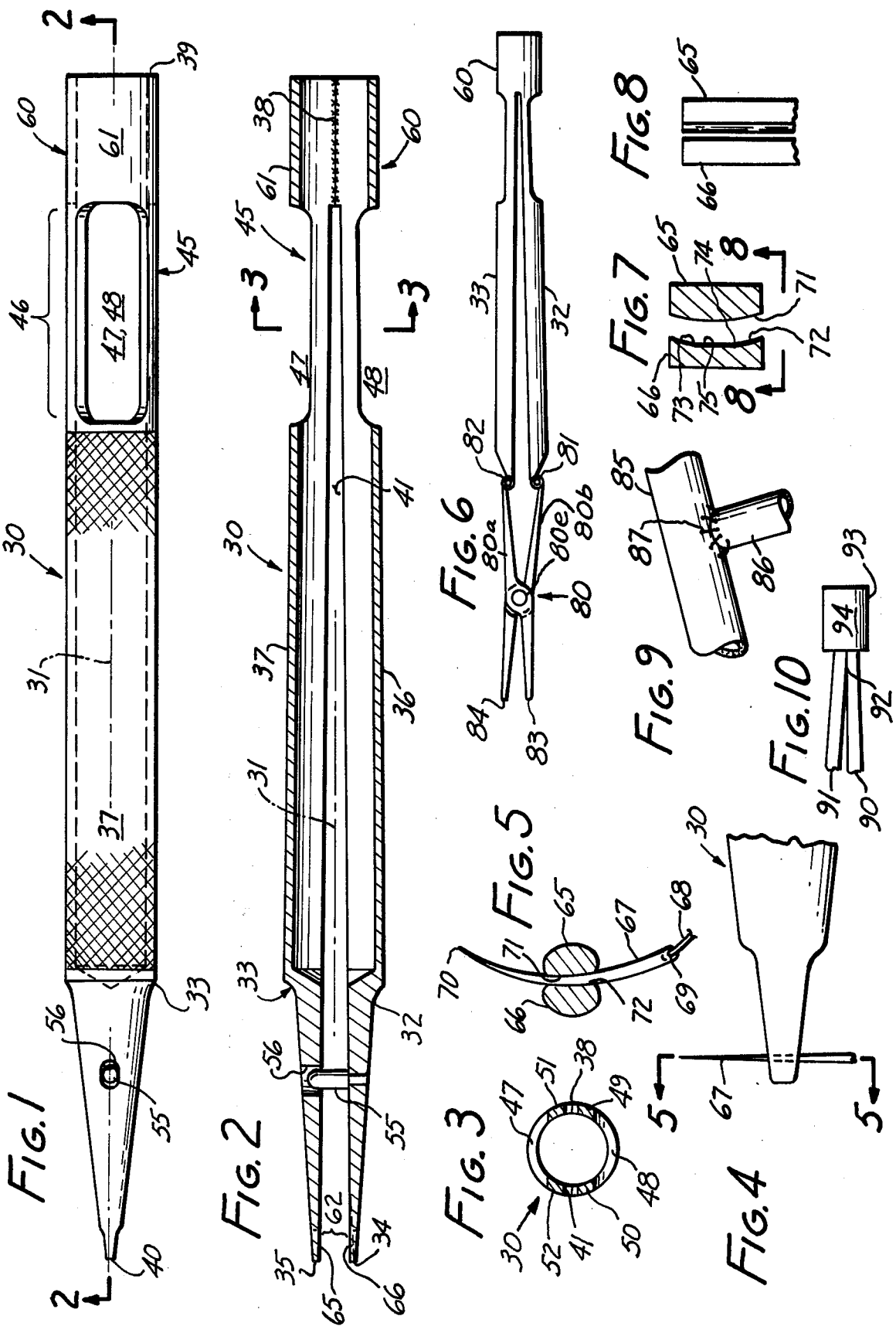

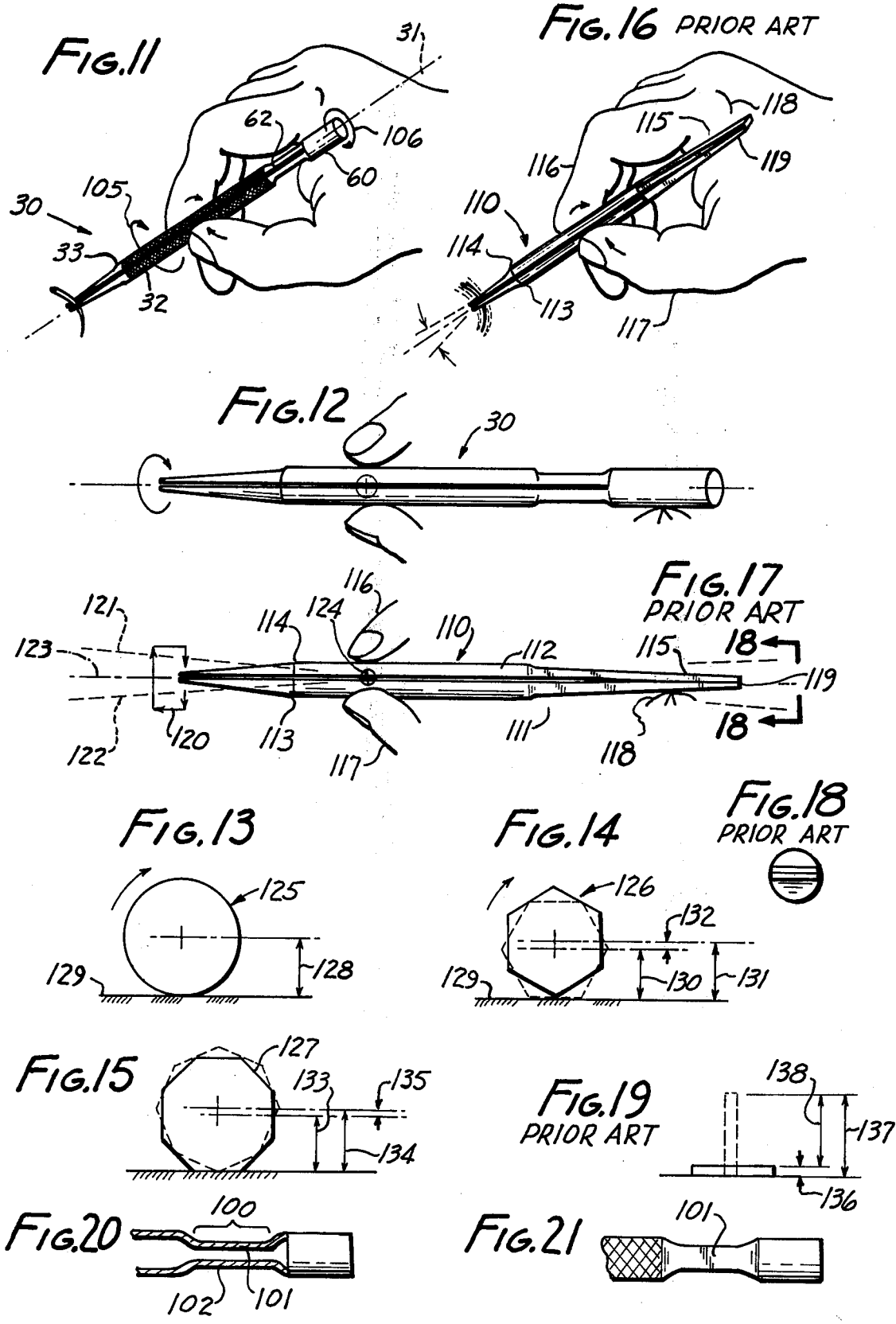

SURGICAL MANIPULATOR

This application relates to a surgical manipulator.

In microsurgery, the surgeon's work is of such fineness that it must be done under microscope magnification, usually between 6 to 40 power. The tissue operated on and the needles and sutures also, are so small that they cannot be manipulated or otherwise treated while held by the surgeon's hand. Instead, they must be held by an instrument, and that instrument is then manipulated in exquisitely small motions. For example, tissue to be cut or sutured is usually held by a pair of tissue holding jaws. A needle is held by a pair of needle-holding jaws. Tissues to be cut are often cut by scissors. Sutures to be cut are often cut by scissors or by nipper jaws. In all of these situations, the jaws are frequently mounted to spring-biased prongs which, when pressed together cause the jaws to do their work. In turn, these prongs form part of a manipulator held by the surgeon and are manipulated by him to do his work.

The viewed area of the operation, and the parts worked on are very small. For example, in one type of operation in the brain, two arteries are joined in a butt-type T-joint wherein one artery has about a one millimeter outer diameter and the other has about a one and one-half millimeter outer diameter. The wall thicknesses are a very small part of these dimensions. To join these arteries together, as many as twelve to fourteen stitches are required, and obviously they are also very small. The needle is usually between about 70 microns and about 150 microns in diameter. The sutures are very fine, known in the art as 10-0 and 11-0 sutures.

It is evident that when doing work under such magnification, even very small lateral movements of the jaws can cause them to miss their mark. Perhaps the tip of the jaws might even move outside of the object field. Therefore the surgeon in order to do his work at all must control his manipulator so the tips of the jaws remain precisely where they belong, no matter what else he may have to do in order to accomplish this.

When conventional manipulators, for example needle holders, are used, the tips of the jaws tend to wobble around the central axis when the manipulator is rotated between the thumb and index finger. The surgeon, who is already extremely preoccupied must make compensatory movements of his hands and arms to hold the tip of his instrument precisely relative to the work. This requires tiring and distracting compensating hand and body movement by the surgeon, which must be accomplished while maintaining a squeeze on the manipulator. In operations which may last between 2 and 10 hours all of this is a source of fatigue, irritation, and tremor, all of which are best minimized or eliminated.

Accordingly, it is an object of this invention to provide a manipulator which is so constructed that when it is rotated around its own central axis there is a minimal or no tendency of the tip of the jaws to wobble laterally. Accordingly, the surgeon is able with confidence to make his rotating manipulations without also having to accomplish compensating maneuvers. The manipulator of this invention therefore does not introduce complications of its own.

A surgical manipulator according to this invention has a central axis with a pair of prongs extending generally axially. Each of these prongs has a first end and a second end. The first ends are connected to one another at a joinder. The second ends are on opposite sides of the axis from each other. Bias means resiliently biases the prongs to move the second ends in opposite directions away from the axis in a plane of flexure which contains the axis. A manipulation surface is provided on each of the prongs, spaced from their point of joinder. A spindle including a knuckle rest surface is provided on the needle holder closer to the joinder than the manipulation surfaces. A jaw is supported by each of the prongs, and these prongs move toward one another when the manipulation surfaces are pressed toward the axis. The manipulation surfaces and the knuckle rest surface are axially spaced from one another so that when the fingers of the surgeon press against the manipulation surfaces, the knuckle rest surface bears against his hand at or near the knuckle at the base of his index finger. The manipulation surfaces, when the jaws are brought together, form a substantially regular geometric surface circumferential around the axis which is no more out of round than a hexagon. The knuckle rest surface is unsplit and is a substantially regular geometric surface circumferential around the axis and no more out of round than a hexagon.

According to a preferred but optional feature of the invention, the bias means is a springily flexible portion of at least one of the prongs.

According to still another preferred but optional feature of the invention, the jaws are needle holders. At least one of the jaws has a pair of contact points which, when the jaws are closed on a needle, lie in a plane normal to the axis. The surface of the jaws between the points in that plane are radially outwardly recessed from a straight line drawn between the two points, whereby the needle can be pressed down between the two points to assume a curved shape and a unique alignment.

The above and other features of this invention will be fully understood from the following detailed description and the accompanying drawings, in which:

FIG. 1 is a top view of the presently preferred embodiment of the invention;

FIG. 2 is a cross section taken at line 2—2 in FIG. 1;

FIG. 3 is a cross section taken at line 3—3 of FIG. 2;

FIG. 4 is a fragmentary portion of FIG. 1 showing a needle grasped thereby;

FIG. 5 is a cross section taken at line 5—5 of FIG. 4;

FIG. 6 is a side view of another embodiment of the invention;

FIG. 7 is a left hand end view of FIG. 2;

FIG. 8 is a side view of FIG. 7 taken at line 8—8 therein;

FIG. 9 shows two arteries intersecting and connected by sutures which have been installed with the use of the needle shown in FIGS. 4 and 5;

FIG. 10 is a fragmentary side elevation of a modification of the invention;

FIG. 11 shows the device of FIG. 1 in use;

FIG. 12 is a side view of a portion of FIG. 11;

FIGS. 13, 14 and 15 illustrate geometric features of this invention;

FIG. 16 shows a device according to the prior art, and illustrates its disadvantages;

FIG. 17 is a view similar to FIG. 12 showing the prior art and its limitations;

FIG. 18 is an end view taken at line 18—18 in FIG. 17;

FIG. 19 is a geometric illustration of a disadvantage of the prior art compared to the constructions of FIGS. 13, 14 and 15;

FIG. 20 is a fragmentary portion of another modification of the device of FIG. 1;

FIG. 21 is a side view of FIG. 20;

Figure 22:
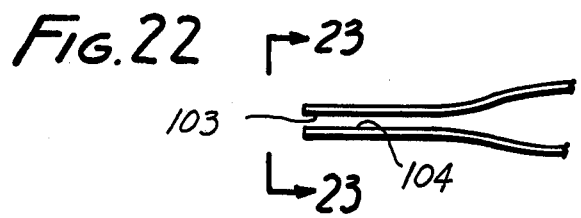
FIG. 22 is a fragmentary side view of another embodiment of the invention.

FIGS. 1, 2 and 6 show the presently preferred embodiment and the best known mode of the invention. FIGS. 1 and 2 show a surgical manipulator 30 equipped to be used as a needle holder. It has a central axis 31 which is generally longitudinal. As best shown in FIG. 2, the manipulator includes a pair of prongs 32, 33. These prongs may be formed separately and later joined together. Alternatively, the device can be manufactured by performing some of the manufacturing steps on a half section of tubing, or flat sheet, then completing the construction of the individual parts, and joining them, such as by welding. With some difficulty, the manipulator can be constructed unitarily, out of a solid rod.

The prongs, in this embodiment, are identical to one another with one exception. Prongs 32 and 33 include respective jaws 34, 35 and manipulation surfaces 36, 37. The prongs are joined together at a joinder 38. If the device is constructed unitarily, the joinder may simply comprise a solid section at the first end 39. The jaws are located at the second end 40. The prongs are at some time split when the device is manufactured by the simplest manufacturing technique. Joinder 38 is a weldment that holds the two prongs together.

A slit is formed between the prongs by removal of metal from each. The prongs are sprung slightly apart so that the tips of their jaws are approximately 3.5 millimeters apart when the manipulator is relaxed. This can be adjusted by deforming the prongs slightly at their joinder.

Bias means 45 may be separate from or integral with the device. In the illustrated embodiment, the bias means is integral with the prongs, and comprises a portion 46 which is springily flexible so as to bias the tips apart as shown but to permit them to be squeezed together by compressive force exerted on the two manipulation surfaces.

In FIG. 1 construction the bias means is formed by a pair of apertures 47, 48 which leave legs 49, 50, 51, 52. These legs have a total cross section area less than the contiguous parts of the prongs, whereby the flexure can occur at the legs by bending them. As an adjunct to maintain alignment, an alignment pin 55 may be carried on the inside of jaw 35 where it will fit into an aperture 56 in the other jaw. The pin makes a fairly close fit with the side walls of aperture 56 as shown in FIG. 1. There is a clearance at the forward and rear walls. This limits or prevents lateral movement of the jaws relative to each other. Except for the pin and aperture, the two prongs are substantially identical.

The manipulator also includes a spindle 60 at the first end. The spindle includes a knuckle rest surface 61.

The shape of the manipulator surfaces and of the knuckle rest surface are of importance to this invention. The manipulation surface is usually knurled to improve the surgeon's grip on the holder. The knuckle rest surface may also be knurled, but usually it will not be. Surfaces which carry knurling or other "roughened" means such as splines or grooves still are within the meaning of the term "surface" as used herein. The outermost portions of the knurling which are contacted by the surgeons hand and fingers will lie in the surfaces yet to be defined. When the prongs are pressed together by compressive force on the manipulation surfaces, the jaws will move toward one another and may or may not close the gap 62 between them. When they reach their nearest approach to one another (for example, when a needle is held between them), they will, except for a small slit, form a substantially regular geometric surface which is circumferential around the axis and which is no more out of round than a hexagon. The spindle is not split, and it is continuous. It also forms a substantially regular surface circumferential around the axis no more out of round than a hexagon. In this condition, the knuckle rest surface and the manipulation surfaces are coaxial.

The more sides the surface has, the closer it approaches a circle. The closer it is to a circle the more effective is the manipulator according to this invention. The geometric considerations involved will be described below. The preferred embodiment of the invention is circularity of all of the surfaces.

Operative elements 65, 66 are supported by the jaws at their free ends. The operative elements are preferably formed as an integral part of the jaws. The operative elements have any desired shaped suited to the intended usage. One usage is for holding a curved needle. For example, FIGS. 4 and 5 show a curved needle 67 to which a suture 68 has been attached by swaging the suture in a hole 69 in the end of the needle. The needle has a pointed end 70 and is inherently arcuate. It is advantageous for this needle to be specifically oriented relative to the jaws, and this is best accomplished by providing one of the operative elements, for example element 65, with a convex surface 71, and element 66 with a concave surface 72. The best curvatures are about the same as those of the relaxed needle to be held by the holder.

Other configurations for the same purpose are useful. For example, concave surface 72 could be formed on element 66 and element 65 might merely be narrower or flat. The ultimate limitation is that the concave surface should have two points of contace 73, 74 (FIG. 7) and the space between them should be relieved radially outward from a straight line 75 drawn between these two points. Then the shape of the other surface is relatively immaterial, provided that it presses against the needle between the two points and does not eliminate the curvature of the needle. A needle holder shaped as described will hold a curved needle in a precise orientation, and prevent it from rotating or tilting.

Figure 24:
FIG. 24 is a fragmentary left hand view of FIG. 6.

The manipulator of FIGS. 1 and 2 has its operative element integral with its jaws, and the jaws are integral with the prongs. FIG. 6 shows that an operative element can be a separate item joined to the jaw. For example, in FIG. 6, the operative element includes a scissors linkage 80 connected to the jaws. The scissor linkage is comprised by two crosslinks 80a, 80b pivotally joined by a pivot 80e. An end of each crosslink is mounted to an end of a respective prong by a respective hinge 81, 82. This has the advantage of a force-multiplying feature, because the scissor linkage can be designed with a lever ratio that will multiply the force applied at its cutting edges. The two prongs are shown supporting the scissors linkage by pivot pins 81, 82. Operative elements 83, 84 on the linkage can be shaped as scissor blades (FIG. 24), or can be formed as nippers, tissue holders, plate-like tweezers, or needle holders. This arrangement provides a marked improvement when coupled with standard implements wherein the angular opening of the jaws is relatively large. The longer manipulator can provide at its ends a lateral compression to produce a large-angle closure of a relatively shorter scissors, for example. Not only does this increase the force exerted on the operative element, but it also provides the basic alignment advantages of this invention. The term "scossors linkage" as used herein means two pivoted crossed members. It is not limited to a cutting apparatus, but can carry any of the types of operative elements just described. It forms a part of the operative element.

FIG. 9 shows a pair of blood vessels 85, 86 joined together in a T-butt joint by means of an operation now performed in the human brain wherein artery 85 has an outside diameter of approximately 1.5 millimeters and artery 86 an outside diameter of approximately 1.0 millimeters. Approximately twelve sutures 87 are used in this small region. They are formed from the suture material 68 attached to needle 67. This operation is conducted in a microscopic field. The desirability for the tip of the manipulator to remain laterally stable should be evident from a consideration of this figure.

FIG. 10 shows a pair of prongs 90, 91 according to FIG. 1 joined at a joinder 92. The construction to the left of the joinder. in FIG. 10 is identical to that in FIG. 1. What is different is that a spindle 93 having knuckle rest surface 94 identical to that of surface 61 is placed over the end of the holder. Prior art devices often have a flat tweezer-like end (see FIGS. 16-18), and this spindle provides a means to provide the benefits of this invention to prior art devices.

FIGS. 20 and 21 show a modification of the bias means of FIGS. 1 and 2. The illustrated portion 100 can be substituted for portion 46 of the FIG. 1 device. Portion 100 includes one flat springy leg 101, 102 for each prong, instead of a pair of legs for each prong. The planes of legs 101 and 102 lie normal to the plane of flexure, which is the plane of FIGS. 2 and 20. This will tend to inhibit lateral movement of the prongs. With this exception the device of FIGS. 20 and 21 are identical to that of FIGS. 1 and 2.

Figure 23:
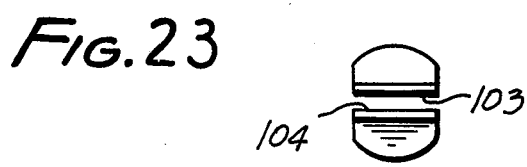
FIG. 23 is a left hand end view taken at line 23—23 in FIG. 22.

FIGS. 22 and 23 show the use of flat plate-like surfaces 103, 104 for use as the operative elements on any of the embodiments. These can be used for a tissue holder, for example. Other shapes such as nippers can also be used. Also, a tooth or teeth can be added to either or both of surfaces 103, 104 to engage and bite into tissue, thereby comprising a toothed tissue holder.

FIGS. 11-19 illustrate the advantages of this invention over the prior art. When this manipulator is used as a needle holder, for example, the needle is grasped by the operative element as shown. For this purpose the surgeon's fingers press against the two manipulation surfaces 36 and 37. The construction of this devide is such that when the manipulator is properly held by the thumb and index finger, the spindle, and especially its knuckle rest surface bears against the knuckle at the base of the first finger or as close thereto as is convenient to the surgeon. The term "knuckle" as used herein is defined to include the muscle pad between the thumb and the index finger, and the side of the knuckle of the index finger.

Especially when the alignment means is utilized, the compressive force can be exerted from substantially any direction around the axis of the device and will still serve to hold the surfaces properly against the needle. The alignment means can, however, be eliminated by stiffening the prongs and the joinder against lateral flexure. With the needle properly held, the surgeon can simply rotate the needle holder between his thumb and index finger to rotate the needle. The rotation adjacent to the fingers is shown by arrow 105, and adjacent to the knuckle by arrow 106. When these rotations are coaxial on axis 31 and the surfaces are circular there will be no lateral motion or wobble of axis 31, and the jaws and the operative elements will remain stationary in the field. Substantially circular manipulation surfaces are known in the art, but not to the inventor's knowledge in combination with substantially round and unsplit knuckle rest surfaces. Similar manipulation is accomplished for holding tissue, for nipping sutures, and for cutting tissue. The appropriate operative elements will be used for the specific manipulation.

A conventional manipulator is shown in FIG. 16. FIG. 16 illustrates a needle holer 110. It includes manipulation surfaces 111, 112 which are conventionally either circular, hexagonal or rectangular. However, at the knuckle end the prongs 113, 114 are conventionally joined at a flat end 115 like common tweezers. This is also illustrated in FIGS. 17 and 18. Now compare FIGS. 12 and 17 where finger 116 and thumb 117 are shown together with a portion of knuckle 118. FIG. 12 illustrates the invention, and shows that the twirling rotation is straight and unwobbling as in FIG. 11. However in FIG. 17, the reaction of the knuckle rest surface 119 on the knuckle causes angular tilting of the axis that creates a somewhat squarish tip path 120 as shown in FIG. 17. Lines 121, 122 schematically show the lateral deflection of the free end from axis 123 caused by the use of prior art manipulators. This tilting principally occurs around point 124 between the thumb and the finger. It is quite pronounced, and the motion is such that the surgeon must compensate for it during his own manipulations by moving his hand and shoulders. It inhibits precision and is distracting, and can cause an undesirable tremor when combined with the need for him to keep the prongs compressed toward one another.

FIGS. 13, 14 and 15 respectively show a round knuckle rest surface 125, a hexagonal knuckle rest surface 126 and an octagonal knuckle rest surface 127. The dimension arrow 128 in FIG. 13 shows that the reaction of the knuckle rest surface with the knuckle 129 causes no lateral movement. In FIG. 14 the arrows 130, 131 show that there is a difference in the spacing of the axis from the knuckle as a function of rotational positions. The increment 132 between dimensions 130 and 131 illustrates the size of the lateral movement. In FIG. 15, an octangonal shape is shown. Arrows 133 and 134 show the extreme positions of the axis relative to the knuckle. Increment 135 being their difference. It will be observed that for approximately the same size device the increment is smaller with the octagonal construction of FIG. 15 than with the hexagonal device of FIG. 14. The larger the number of sides, the smaller will be the increment. There is no "increment" for a circular device. The inventor has found that a square or rectangular construction does not give suitable results, and that the knuckle rest surface, and preferably also the manipulation surfaces, should not be more out of round than a regular hexagon. There may be any number of sides greater than six, and preferably they will be round. Instead of truly round the surfaces may be knurled or splined, but the results should always be such that the rotation of the device past the knuckles and between the thumb and finger should result in no more lateral movement than that developed from the rotation of a regular hexagon.

FIG. 19 shows the prior art performance of a rectangular tweezer-like construction. Arrows 136, 137 show the two extreme positions relative to the knuckle. The increment 138 between them is quite large. It is this increment which causes the erratic path illustrated in FIG. 17.

The manipulator is best made of high grade surgical steel The flexible portions are formed by suitably reducing the pertinent dimensions. If preferred, the prongs can be pivotally joined and biased apart by springs, but this type of construction is more difficult to clean and to sterilize than the integral constructions illustrated.

This invention thereby provides a manipulator which permits the surgeon to manipulate an operative element, by a rotating action of the thumb and index finger with inherent axial stability.

There are manipulators in existence wherein a knuckle rest surface exists which is split and which leaves a spacing between them during operation. Such a obliquity approaches an elliptical or oblong shape, and produces the same mischief as is illustrated in FIG. 19. The knuckle rest surface should be unsplit and regular.

This invention thereby provides a means for enabling the surgeon to manipulate an operative element without himself having to compensate for lateral movements caused by the manipulator which carries the operative element. This is a substantial advantage in microsurgery, and minimizes the stress and frustration of the surgeon.

This invention is not to be limited by the embodiments shown in the drawings and described in the description which are given by way of example and not of limitation, but only in accordance with the scope of the appended claims.

I claim:

1. A surgical instrument having a central axis, comprising a pair of prongs, each having a first end and a second end, said first ends being integrally connected to one another at a joinder, said second ends being on opposite sides of said axis;

bias means resiliently biasing said prongs to move said second ends in opposite directions away from said axis in a plane of flexure which includes said axis;

a manipulation surface on each of said prongs spaced from said point of joinder;

a spindle including a knuckle rest surface on said instrument closer to the joinder than the manipulation surface;

a pair of jaws on the prongs which move toward one another when the manipulation surfaces are pressed toward one another;

a hinge carried by each of said jaws;

a pair of crosslinks joined by a pivot between their ends to form a scfissor-type linkage, one of the ends of each of the crosslinks being joined to a respective one of said hinges;

an operative element carried by each of said crosslinks farther from the prongs than the pivot;

the manipulation surfaces and the knuckles rest surface being axially spaced from one another so that when the thumb and index finger of the surgeon press against respective manipulation surfaces, the knuckle rest surface bears against his hand near the knuckle at the base of his index finger, the manipulation surfaces, when the jaws are brought toward one another, forming a substantially regular geometric surface circumferential around the axis and no more out of round than a hexagon, the pressing together of the manipulator surfaces causing the scissor linkage to close to move the operative elements relative to one another, the knuckle rest surface being a continuous, substantially regular geometric surface circumferential around the axis and no more out of round than a hexagon.

2. A surgical instrument according to claim 1 in which the bias means is a springily flexible integral portion of at least one of the prongs.

3. A surgical instrument according to claim 2 in which the said portion constitutes a reduced lateral cross section of the prongs.

4. A surgical instrument according to claim 2 in which the said portion is a flat springy leg lying substantially normal to the plane of flexure.

5. A surgical instrument according to claim 2 in which the said portion comprises two springy legs on the same prong which are laterally spaced apart from one another.

6. A surgical instrument according to claim 1 in which alignment means is formed on said prongs to constrain the prongs to movement in the plane of flexure.

7. A surgical instrument according to claim 6 in which said alignment means comprises a post on one of said prongs and an aperture in the other of said prongs adapted closely to receive the post and prevent skew movement of the prongs.

8. A surgical instrument according to claim 1 in which said knuckle rest surface and manipulation surfaces are hexagons.

9. A surgical instrument according to claim 1 in which the said knuckle rest surface and manipulation surfaces are octagons.

10. A surgical instrument according to claim 1 in which the said knuckle rest surface and manipulation surfaces are round.

11. A surgical instrument according to claim 10 in which the manipulation surfaces are knurled.

12. A surgical instrument according to claim 11 in which the bias means is a springily flexible portion of at least one of the prongs.

13. A surgical instrument according to claim 1 in which said operative elements form a needle holder.

14. A surgical instrument according to claim 1 in which said operative elements are scissor blades.

* * * * *